US00PP09567P

United States Patent [19]

Moore

[11] Patent Number: Plant 9,567

[45] Date of Patent: Jun. 4, 1996

[54] CLIMBING FLORIBUNDA ROSE PLANT NAMED 'MORCLIP'

[76] Inventor: Ralph S. Moore, 2519 E. Noble Ave., Visalia, Calif. 93292

[21] Appl. No.: 382,520

[22] Filed: Feb. 2, 1995

[51] Int. Cl.[6] ..... A01H 5/00

[52] U.S. Cl. ..... Plt./27

[58] Field of Search ..... Plt./2, 5, 6, 22, Plt./27, 26

[56] References Cited

U.S. PATENT DOCUMENTS

P.P. 6,468 12/1988 Moore ..... Plt./26

*Primary Examiner*—Howard J. Locker

[57] ABSTRACT

This invention relates to a new and distinct cultivar of floribunda rose, primarily identified by its vigorous climbing habit and its large (single) flowers with petals being medium to deep pink.

2 Drawing Sheets

The present invention relates to a new and distinct cultivar of hardy, climbing type rose plant of the floribunda class. The cultivar being primarily characterized as to novelty by its vigorous climbing habit and by the few petaled (single) pink flowers.

The cultivar is further characterized by:

An abundance of bloom, with flowers usually borne several to the stem in loose clusters or sprays on tips of climbing shoots and on laterals.

Slight fragrance.

A plant of vigorous, climbing growth habit, with semi-glossy pointed leaflets; the buds and flowers being similar in form and color to 'MORplag' (Playgirl).

A plant which grows and blooms satisfactorily outdoors; with repeat bloom, is good for growing in the garden on fence or trellis and provides excellent garden decoration as well as cut flowers for bouquets and exhibition.

The present cultivar of floribunda rose is a climbing sport of the rose 'MORplag' (Playgirl) (U.S. Plant Pat. No. 6,468) which was discovered by me at my nursery, located at Visalia, Calif., as a natural sport (mutation) on a plant of the bush variety (cultivar) then growing on my property.

Subsequent to my discovery of the sport I successfully asexually reproduced this new cultivar at my nursery, located as aforementioned, by budding as well as by cuttings; the reproductions have run true in all respects.

The color photographs illustrate the cultivar including the foliage, buds and flowers.

Figure 1:
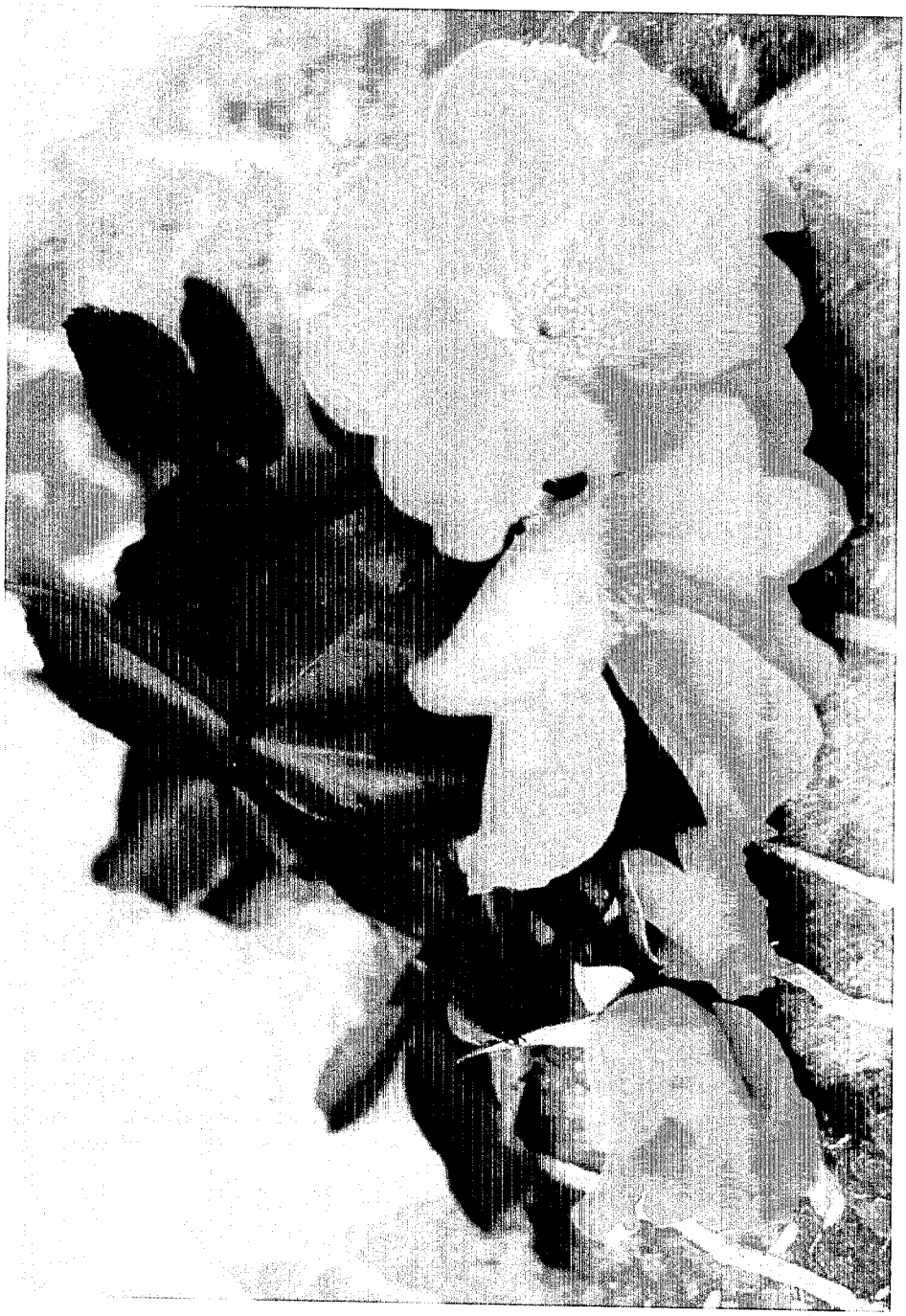
FIG. 1 shows open flower with stamens, also deeper colored partly open buds.
Figure 2:
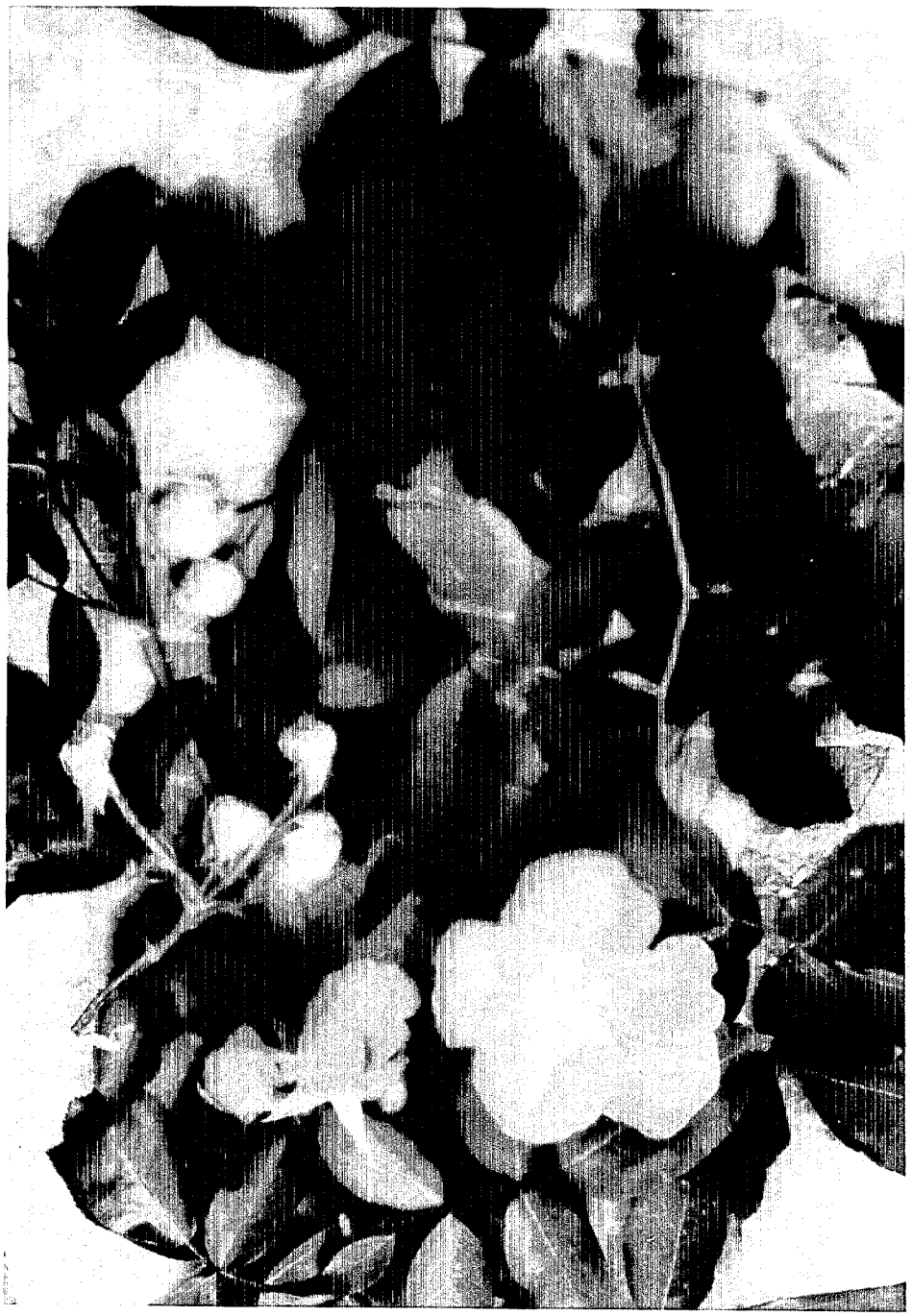
FIG. 2 shows open flower, buds, foliage, ripe (orange) hips and a short section of climbing cane.

Plant part coloration illustrated is as true as is reasonably possible to attain in photographic illustrations of this type.

Referring now specifically to the new and distinct cultivar of climbing floribunda rose plant, the following is a detailed description thereof in outline; all major color plate identification being by reference to the *British Colour Council Horticultural Colour Chart,* except where common terms of color definition are employed.

Type: Hardy; climbing; sport; outdoors; cut flowers; garden decoration; exhibition.

Class: Floribunda.

*Variety identification.*—'MORclip'.

*Commercial synonym.*—Climbing Playgirl.

Flowers borne: Usually several together (3 to 5 or more) on sturdy, wiry stems.

Quantity of bloom: Abundant.

Bud:

*Peduncle.*—Medium to long (3.7 cm–4.5 cm); slender but sturdy; erect; medium green, mear Willow Green 000862, sometimes tinted bronze (outdoors); usually quite smooth.

*Before calyx breaks.*—Size-medium (18 mm–20 mm long).

*Form.*—Long pointed, with few foliaceous appendages and hairs on surface of bud; with foliaceous parts extending beyond the tip of the bud equal to less than one-half its length.

*Color.*—Medium green, near Willow Greern 000862, occasinoally tinted with bronze (outdoors).

*As calyx breaks (sepals turn down).*—Color — deep pink to red, (near Cardinal Red 822/1. Yellowish at base).

*Opening.*—Opens well in all weather.

Bloom:

*Size when fully open.*—Large, averaging about 9 cm (3½").

*Petalage.*—Few — averaging about 5 to 7 petals, arranged regularly.

*Form.*—Open, with slightly ruffled petals. Open flowers show stamens.

*Sepals.*—Permament; spear shaped; recurved.

Petals: Fairly thick; satiny on inside and on outside surface.

*Shape.*—Outside petals — broad lanceolate (nearly round) with rounded tip, the petals being wavy (Sweet Pea-like) with often serrated edges. '*Color.*—Newly opening flower — Outside petal — Outside surface — near Tyrian Rose 24 with lighter and darker streaks (veining); with small yellow area at base. Inside surface — near Tyrian Rose 24 or Spirea Red 025 with lighter veining; with bright yellow area at base. More mature, fully opened flower — Outside surface — near Tyrian Rose 24/1 with small whitish flecks or streaks. Inside surface — near Tyrain Rose 24/1 with lighter veining or flecks becoming whitish at base. In warmer weather and brighter light — buds and flowers are ligher in color.

*General color effect.*—Newly opened flowers — Deep pink. Three days open — color is similar to fresh open flower, but less bright.

*Behavior.*—opens well in all weather. Spent petals or flowers drop off. Flower longevity on plant growth outdoors in July and August in Visalia, Calif. — 5 to 6 days or longer. Cut flowers at living room temperature last 3 to 5 days.

Reproductive organs:

*Stamens.*—Many.

*Filaments.*—Slender; reddish.

*Anthers.*—Well formed, yellow.

*Pollen.*—Fairly abundant, yellow.

*Pistils.*—Numerous.

*Styles.*—Fairly uniform; yellowish; bunched.

*Ovaries.*—All enclosed in calyx.

*Hips.*—Several. Rounded, 15 mm in diameter. Color — Orange.

Foliage:

*Leaves.*—Compound of five (sometimes 3 or 7) leaflets; large (up to 16 cm long by 12 cm wide); leathery; semi-glossy to glossy.

*Leaflets.*—Shape: Broad lanceolate; apex acute; base — rounded. Color: Top surface — near Sage Green 000861. Lower surface — near Willow Green 000862. Rachis: Medium strength; upper side may have a few short hairs; grooved; underside may have several small thorns (or claws) and a few to several tiny short prickles. Stipules: Short length; medium width; medium to short length narrow points which turn out usually at about 45° or less. Color similar to leaflets.

*Habit.*—Climbing; canes or shoots may reach 2.5 m (7' to 8' or more).

*Growth.*—Vigorous; internodes fairly short.

*Canes.*—Medium slender; sturdy.

*Main stems.*—Color: Medium green, near Willow Green 000862.

*Throns.*—Average (few to none or some canes), of medium size and length usually straight Hairs — few to none.

The floribunda rose plant and its flowers as heretofore described may vary in slight detail due to climate, soil and cultural conditions under which the cultivar may be grown; the present description being of the cultivar as grown at Visalia, Calif.

The following is claimed:

1. A new and distinct cultivar of rose plant of the floribunda class, of hardy, much branched, climbing habit substantially as illustrated and described, with flowers of an unusual pink/lavender blend coloring, the buds and flowers being similar in form and color to the bush variety 'MORplag' of which this is a natural sport, with the open flower being single with 5 to 7 wavy petals, and further characterized by a plant of vigorous, upright shape with main stems and shoots of moderate thorniness, the said plant being easy to propagate from soft-wood cuttings and by budding with an abundance of large, semi-glossy to glossy foliage, the flowers being usually borne in loose clusters on medium length stems.

* * * * *